(12) United States Patent
Tsuda et al.

(10) Patent No.: US 8,568,710 B2
(45) Date of Patent: Oct. 29, 2013

(54) PLANT DISEASE CONTROLLING AGENT AND CONTROLLING METHOD

(75) Inventors: Kazuhisa Tsuda, Kameoka (JP); Yoshitaka Kosaka, Kameoka (JP); Mitsunobu Kataoka, Kyoto (JP)

(73) Assignee: Meiji Seika Pharma Co., Ltd., Tokyo (JP)

( * ) Notice: Subject to any disclaimer, the term of this patent is extended or adjusted under 35 U.S.C. 154(b) by 1525 days.

(21) Appl. No.: 11/658,544

(22) PCT Filed: Jul. 28, 2005

(86) PCT No.: PCT/JP2005/013872
§ 371 (c)(1),
(2), (4) Date: Jan. 24, 2007

(87) PCT Pub. No.: WO2006/025167
PCT Pub. Date: Mar. 9, 2006

(65) Prior Publication Data
US 2009/0169530 A1    Jul. 2, 2009

(30) Foreign Application Priority Data
Jul. 29, 2004  (JP) ................................ 2004-222576

(51) Int. Cl.
*A01N 63/00* (2006.01)
*C12N 1/20* (2006.01)

(52) U.S. Cl.
USPC ..................................... 424/93.45; 435/252.1

(58) Field of Classification Search
None
See application file for complete search history.

(56) References Cited

U.S. PATENT DOCUMENTS 5,378,458 A * 1/1995 Mayra-Makinen et al. . 424/93.3
5,833,977 A * 11/1998 Relander ...................... 424/93.3
6,322,782 B1 * 11/2001 Walker et al. ................ 424/93.4

FOREIGN PATENT DOCUMENTS

| JP | 5-000916 | 1/1993 |
|---|---|---|
| JP | 6-009325 | 1/1994 |
| JP | 6-107511 | 4/1994 |
| JP | 10-164987 | 6/1998 |
| JP | 11-106306 | 4/1999 |
| JP | 2001-333766 | 12/2001 |
| JP | 2003-277212 | 10/2003 |
| JP | 2003-300803 | 10/2003 |
| JP | 2004-135669 | 5/2004 |

OTHER PUBLICATIONS

Magnusson et al., FEMS Microbiology Letters 219 (2003) 129-135.*
Jan. 18, 2007 Ronel Visser, et al.; "Antagonism of Lactic Acid Bacteria against Phytopathogenic Bacteria"; Applied and Environmental Microbiology, 1986, vol. 52, No. 3, pp. 552-555.
Jan. 18, 2007 A. Laitila, et al.; "Antifungal Activities of two *Lactobacillus plantarum* strains against Fusarium moulds ni vitro and in malting of barley"; Journal of Applied Microbiology, 2002, vol. 93, No. 4, pp. 566-576.
Skyttae, Eija et al.; "Production and characterization of antibacterial compounds produced by *Pediococcus damnosus* and *Pediococcus pentosaceus*", Journal of Applied Bacteriology, 1993, vol. 74, No. 2, pp. 134-142.

* cited by examiner

*Primary Examiner* — Irene Marx
(74) *Attorney, Agent, or Firm* — Jordan and Hamburg LLP

(57) ABSTRACT

A plant disease controlling agent containing a lactic acid bacterium which is capable of controlling plant disease and a plant disease controlling method which comprises treating a plant and/or soil with the above-mentioned lactic acid bacterium. By using the lactic acid bacterium seemingly advantageous to human health, an agricultural crop can be safely and stably produced. As the lactic acid bacterium as mentioned above, use may be favorably made of a microorganism belonging to the genus *Pediococcus* such as *Pediococcus pentosaceus* or a microorganism belonging to the genus *Lactobacillus* such as *Lactobacillus plantarum*.

4 Claims, No Drawings

PLANT DISEASE CONTROLLING AGENT AND CONTROLLING METHOD

BACKGROUND OF THE INVENTION

The present invention relates to a controlling agent and a controlling method for plant disease and, more particularly, it relates to a controlling agent and a controlling method for plant disease where a lactic acid bacterium seemingly advantageous to human health is used whereby disease of agricultural crop is able to be suppressed. The invention also relates to a treating method for plant and/or soil using the specific lactic acid bacteria.

In recent years, application of biological control which is a control using a useful microorganism has been investigated to plant diseases which are difficult to control by synthetic agricultural chemicals. There has been also a strong demand for agricultural methods considering in environments or, in other words, agriculture of an environment conservation type (sustainable agriculture) and a biological control using a useful microorganism has been positively investigated with an object of suppression of use of chemically synthesized agricultural chemicals.

For example, in the following Patent Documents 1 to 3, control techniques for plant diseases using microorganisms belonging to the genus *Pseudomonas* are proposed. In the following Patent Document 4, there is a proposal for a technique of controlling the plant diseases by the joint use of an actinomycete having an antagonistic property to causing microorganism for soil disease and a microorganism producing viscous substances. In the following Patent Document 5, there is a proposal for controlling the plant diseases by the joint use of a microorganism belong to the genus *Cladsporium* and a microorganism belong to the genus *Bacillus*.

Patent Document 1: Japanese Patent No. 3,431,926 (JP-A-5-916)
Patent Document 2: Japanese Patent No. 2,533,828 (JP-A-6-9325)
Patent Document 3: Japanese Patent No. 3,135,708 (JP-A-6-107511)
Patent Document 4: JP-A-2003-277212
Patent Document 5: JP-A-2003-300803
Patent Document 6: JP-A-10-164987

When a microorganism used for a purpose of control of plant diseases is sold by indicating its control effects, it is necessary to register it as agricultural chemicals in accordance with the Agricultural Chemicals Regulations Law of Japan. In the registration of agricultural chemicals, examinations for safety such as evaluation of influence to human, animals/plants and natural environment are essential in addition to a control effect on plant diseases, and only the microorganism which passes the examinations is able to be registered and sold as agricultural chemicals.

Further, under the circumstance where interest of consumers in safety of "food" is increasing, interest is also paid to a microorganism in food, and consideration in such a point is also an important problem in agricultural crop which is subjected to a disease control utilizing the useful microorganism.

On the other hand, in view of an increase in consciousness of "health" by consumers, functional components useful to human body and food containing such components are becoming popular. Among them, public interest is also increasing in lactic acid bacteria which are said to have effects such as a calming action to intestinal disorder and a suppressive action to cancer.

Under such circumstances, if diseases of agricultural crop are able to be controlled using a lactic acid bacterium which is said to be useful for human health, no problem in a safety examination for the registration of agricultural chemicals is resulted, anxiety of consumers to safety is cleared away and, further, properties in function and as commercial product of the agricultural crop are enhanced whereby that will become an ideal control of diseases.

The present invention has been achieved in view of the above and its object is to provide a controlling agent and a controlling method for plant disease using a lactic acid bacterium which is seemingly advantageous to human health as well whereby production of agricultural crop in safe, assured and stable manner is now possible.

In the aforementioned Patent Document 6, there is a proposal of a cultivating technique for plant. This technique relates to a cultivating method where cultivating environment is able to be artificially controlled in a cultivating process from the stage of seeds to the stage where shipping is possible (such as hydroponics). In the method, after plant is washed, a lactic acid bacterium as a microorganism which is non-toxic to human body is fixed on the surface of the plant and the plant surface is covered by the lactic acid bacterium whereby invasion and proliferation of miscellaneous microorganisms and pathogenic microorganisms are suppressed. However, this technique relates to a food preservation technique called biopreservation and the lactic acid bacterium used is for such a purpose that plant such as white radish sprout is not polluted by microorganism which is harmful to human (such as *Escherichia coli*). Therefore, that is a technique which is clearly different from the present invention where cultivation in a farm under the environment in which numerous microorganisms are present is main and a lactic acid bacterium is used for controlling the plant disease which is a disease of plant itself.

In the Patent Document 4, use of a microorganism belonging to the genus *Lactobacillus* is disclosed but this microorganisms is mentioned in such a manner that the microbe itself has no control effect on plant diseases but it is a microorganism producing a viscous substance jointly used with actinomycete which is an antagonistic microorganism. Accordingly, this document does not suggest that a lactic acid bacterium has a control effect on plant diseases such as soil disease.

SUMMARY OF THE INVENTION

The present inventors have carried out intensive investigations for solving the aforementioned problems and, as a result, they have found that plant diseases of agricultural crop are able to be controlled using lactic acid bacteria which has been said to be useful for human health, and achieved the present invention.

Thus, the present invention relates to a controlling agent for plant disease which is characterized in containing a lactic acid bacterium having a controlling ability to plant disease. The invention also relates to a controlling method for plant disease which is characterized in treating plant and/or soil by a lactic acid bacterium having a controlling ability to plant disease.

The invention further relates to a method for treating plant and/or soil by at least one type of a lactic acid bacterium selected from the group consisting of *Pediococcus pentosaceus* FERM BP-10365 strain and *Lactobacillus plantarum* NITE BP-108 strain.

According to the invention, plant disease of agricultural crop is controlled using a lactic acid bacterium and, therefore, stable agricultural crop production is now possible together with keeping a high safety. In addition, since a lactic acid bacterium is used for the treatment, when it is in symbiosis in a high density in agricultural crop, it has a possibility of being able to give function such as a controlling action for intestinal disorder and a suppressive action for cancer to agricultural crop and it is also possible to enhance the commercial value of the agricultural crop.

Further, the aforementioned FERM BP-10365 strain and NITE BP-108 strain have an effect of enhancing the germination rate of seeds under an environmental stress condition as well as a control effect on plant diseases and, therefore, the aforementioned treating method using the microorganisms as such is able to be utilized not only as a method for controlling the plant diseases but also as a method for improving the germination.

DETAILED DESCRIPTION OF THE INVENTION

Now the invention will be illustrated in detail as hereunder.

With regard to a lactic acid bacterium used for controlling the plant disease in the invention, there is no particular limitation so far as it has an ability of preventing the infection of plant by a pathogenic microorganism or, in other words, a preventive ability to plant disease. The disease-controlling ability may be by any action of antibiotic action, competitive action and resistance-inducing action or by a combination of two or more actions thereof. The antibiotic action is an action where a lactic acid bacterium produces an antibiotic substance and a pathogenic microorganism is suppressed by that and is also called an antagonistic property. The competitive action is an action where a lactic acid bacterium scrambles for spaces or nutritive components with a pathogenic microorganism and growth of a lactic acid bacterium is brisk whereby the bacterium firstly occupies the space or firstly takes up the nutrients so that the pathogenic microorganism is suppressed. The resistance-inducing action is an action where a lactic acid bacterium firstly acts on the plants and infection and growth of pathogenic microorganism are suppressed by the substance produced thereby.

The lactic acid bacterium used in the invention is that which satisfies the conditions that (1) it is gram-positive, (2) its cell form is *bacillus* or *coccus*, (3) it is negative to catalase, (4) it produces 50% or more lactic acid to consumed glucose, (5) it does not form endogenous spores and (6) it has no motility or rarely shows motility.

Specific examples are microorganisms belonging to the genus *Pediococcus* such as *Pediococcus pentosaceus, Pediococcus acidilactici, Pediococcus parvulus, Pediococcus damnosus* and *Pediococcus halophilus*; to the genus *Lactobacillus* such as *Lactobacillus mali, Lactobacillus suebicus, Lactobacillus plantarum, Lactobacillus alimentarius, Lactobacillus sakei, Lactobacillus pentosus, Lactobacillus brevis, Lactobacillus malefermentans, Lactobacillus lactis, Lactobacillus gasseri, Lactobacillus acidophilus, Lactobacillus bulgaricus* and *Lactobacillus casei*; to the genus *Lactococcus* such as *Lactococcus lactis, Lactococcus raffinolactis* and *Lactococcus plantarum*; to the genus *Carnobacterium* such as *Carnobacterium divergens*; to the genus *Weissella* such as *Weissella minor*; to the genus *Atopobium* such as *Atopobium parvulus*; to the genus *Streptococcus* such as *Streptococcus bovis*; to the genus *Entercoccus* such as *Enterococcus avium*; to the genus *Vagococcus* such as *Vagococcus fluvialis*; to the genus *Leuconostoc* such as *Leuconostoc mesenteroides* and *Leuconostoc lactis*; to the genus *Oenococcus* such as *Oenococcus oeni*; and to the genus *Tetragenococcus* such as *Tetragenococcus halophilus*. Each of them may be used solely or plural microorganisms belonging to the same genus or different genus may be used jointly.

Preferred ones are microorganisms belonging to the genus *Pediococcus* or the genus *Lactobacillus*. More preferred one is at least one microorganism selected from the group consisting of *Pediococcus pentosaceus, Pediococcus acidilactici, Lactobacillus plantarum, Lactobacillus alimentarius* and *Lactobacillus sakei*. A KMC05 strain (FERM BP-10365 strain) belonging to *Pediococcus pentosaceus* and an SHH15 strain (NITE BP-108 strain) belonging to *Lactobacillus plantarum* are particularly good in a control effect on plant disease as shown in Examples which will be mentioned later and, therefore, it is preferred to use them.

In addition, in the case of those KMC05 strain and SHH15 strain, improvement in germination rate of seeds under an environmental stress condition is available as shown in the Examples which will be mentioned later and, therefore, they are able to contribute in healthy and stable germination and growth of seeds together with a control effect on plant disease. Accordingly, the microorganisms are able to be utilized not only for a controlling method of plant disease but also to an improving method for germination. When they are utilized as an improving method for germination, the microorganisms are applied to seeds or applied to the soil before or after sowing.

There is no particular limitation for a plant disease which is an object of the control according to the invention and the invention is able to be applied to controlling of various kinds of plant diseases including soil disease. Examples thereof are wilt, soil rot (damping-off), foot rot, verticillium wilt, leaf spot, clubroot, phytophthora blight, white rust, downy mildew, rust, violet root rot, southern blight, powdery mildew, anthracnose, gray mold rot, blast, soft rot, bacterial wilt, bacterial rot, surface rot, bacterial leaf spot, root tumor and scab which are generated, for example, in a chenopodiaceae plant such as spinach, a gramineae plant such as rice and corn, an araceae plant such as taro, calla and pothos, a liliaceae plant welsh onion, onion, tulip and lily, a cruciferae plant such as cabbage, Chinese cabbage, Japanese radish, stock and flowering cabbage, a rosaceae plant such as strawberry, Japanese apricot, peaches and apple, a leguminosae plant such as soybean and adzuki bean, an umbelliferae plant such as carrot and parsley, a solanaceae plant such as chill pepper, eggplant, tomato, potato and *petunia*, a cucrubitaceae plant such as cucumber, watermelon and pumpkin, a compositae plant such as edible burdock, lettuce, *chrysanthemum*, cosmos and sunflower, an iridaceae plant such as *gladiolus*, a plumbaginaceae plant such as statice, a gesneriaceae plant such as *saintpaulia*, a scrophulariaceae plant such as snapdragon and *torenia*, a caryophyllaceae plant such as carnation and common *gypsophila*, a convolvulaceae plant such as morning glory, an amaryllidaceae plant such as *narcissus*, an orchidaceae plant such as cattleya and *cymbidium*, an ebenaceae plant such as persimmons, a moraceae plant such as fig, a vitaceae plant such as grapes, a fagaceae plant such as chestnuts, a rutaceae plant such as satsums orange and lemon and an actinidiaceae plant such as kiwi fruit.

Examples of the pathogenic microorganism are filamentous fungi such as the genus *Fusarium*, the genus *Phytium*, the genus *Rhizoctonia*, the genus *Verticillium*, the genus *Alternaria*, the genus *Plasmodiophora*, the genus *Phytophthora*, the genus *Albugo*, the genus *Peronospora*, the genus *Puccinia*, the genus *Hericobasidium*, the genus *Sclerotium*, the genus *Sphaerotheca*, the genus *Colletotrichum*, the genus *Botrytis* and the genus *Pyricularia*; bacteria such as the genus *Erwinia*, the genus *Ralstonia*, the genus *Xanthomonas*, the genus *Clavibacter*, the genus *Pseudomonas* and the genus *Agrobacterium*; and actinomycete such as the genus *Streptomyces*.

The controlling agent for plant disease according to the invention contains the above-mentioned lactic acid bacterium and, with regard to its form, it is a form which is able to be adopted by usual agricultural chemicals such as granules, powders, wettable powders and emulsions and there is no particular limitation therefor. An example is that the aforementioned lactic acid bacterium is provided as powders or granules by adsorbing it with a pharmaceutically acceptable carrier and, in that case, diatomaceous earth, clay, talc, pearlite, chaff or bone powder may be used as a carrier.

The method for the control of plant diseases according to the invention is that the aforementioned lactic acid bacterium is applied to plant or soil and there is no particular limitation for its applying method. For example, the following methods will be listed.

(1) A method in which a liquid where the aforementioned lactic acid bacterium is dispersed such as a culture liquid of the lactic acid bacterium is applied to plant. The method covers spraying of the dispersion of the lactic acid bacterium to seeds or dipping of seeds in said dispersion so that it is applied to the seeds. It also covers dipping of root of seedling with said dispersion before permanent planting, stab inoculation of the dispersion to leaves and stems, etc.

(2) A method in which the aforementioned dispersion of lactic acid bacterium is applied to the soil. It covers spraying, drenching, etc. of said dispersion to the soil for sowing, to the soil for growing of seedling, to the farm, etc. In that case, the dispersion may be applied to the soil before permanent planting of the plant or before sowing of the seeds or may be applied to the soil after permanent planting or after sowing of the seeds.

(3) A method in which a powdery or granular controlling agent prepared by pulverizing the aforementioned lactic acid bacterium itself or prepared by adhering to a carrier is applied to the plant. It covers a method where the powdery or granular controlling agent is applied to the seeds by adhering on the seed surface or mixing with the seeds followed by sowing.

(4) A method in which the aforementioned powdery or granular controlling agent is applied to the soil. It covers a method in which said powdery or granular controlling agent is mixed with the aforementioned various kinds of cultivating soils or with the soil of the farm or is sprinkled over the soil of the farm.

EXAMPLES

The invention will now be more specifically illustrated by way of the following Examples although the scope of the invention is not limited thereto.

Example 1

Control Effect on Fusarium Wilt of Spinach

For a purpose of establishing the technique of controlling the plant disease of spinach using a lactic acid bacterium, a lactic acid bacterium which suppresses Fusarium wilt which is one of soil diseases of spinach was selected as follows.

Firstly, 149 bacterial strains which are presumed to be mainly composed of lactic acid bacteria isolated from fermented milk or fermented foods were subjected to a primary selection. In the primary selection, each bacterium is subjected to a stationary culture on 8 ml of MRS liquid medium at 37° C. for 3 days and then centrifuged at 5,000 rpm for 5 minutes to recover the cells. The recovered cells were washed with sterile water for three times and, in a suspension in a concentration of $10^9$ cfu/ml prepared with sterile water, seeds of spinach (variety name: Okame) in the same amount as the suspension were dipped at 23° C. for 24 hours. After that, the seeds subjected to a dipping treatment were sown in six pots (each pot was a plastic pot of 10.5 cm diameter being filled with commercially available cultivating soil) at the rate of 10 seeds per pot and grown in a greenhouse kept at 20° C. On the tenth day after the sowing, a microorganism for wilt (Ho4 strain of *Fusarium oxysporum*) was inoculated by drenching to each pot so as to make the wilt microorganism concentration $5 \times 10^3$ cfu (colony-forming units) per gram of the soil and grown in a greenhouse of 30° C. for 30 days, and numbers of the diseased seedlings were checked. As a control group, seeds which were dipped in sterile distilled water were used instead of the microorganism suspension. For each microorganism, protective value was calculated by the following formula and 15 strains where protective value was 40 or more were selected as lactic acid bacteria having controlling ability to plant disease. Relation between the protective value and the strain numbers was as shown in the following Table 1.

Protective Value=(1−(Percentage of Fusarium wilt in treatment/(Percentage of Fusarium wilt in control))×100

TABLE 1

| | Protective Value | | | | | | |
|---|---|---|---|---|---|---|---|
| | ≤9 | 10 to 19 | 20 to 29 | 30 to 39 | 40 to 49 | 50 to 59 | ≥60 |
| Strain Numbers | 89 | 23 | 12 | 10 | 6 | 6 | 3 |

The fifteen strains selected in the primary selection were subjected to the secondary selection. In the secondary selection, seeds of spinach subjected to a dipping treatment in a suspension of bacteria by the same method as in the primary selection were sown in four pots (each pot was a plastic pot of 15.0 cm diameter being filled with commercially available cultivating soil so as to make the wilt microorganism concentration $1 \times 10^4$ cfu per gram of the soil) at the rate of 15 seeds per pot, grown in a greenhouse kept at 20° C. for ten days after the sowing and then cultivated in a greenhouse of 30° C. for 30 days thereafter and, on after 40 days from the sowing, numbers of diseased seedlings were checked. As a result, eight strains were selected as lactic acid bacteria effective to Fusarium wilt of spinach and, among them, KMC05 strain which was particularly effective to Fusarium wilt was selected. Percentage of Fusarium wilt and protective value of KMC05 strain was as shown in the following Table 2.

TABLE 2

| Treatment | Percentage of Fusarium wilt (%) | Protective Value |
|---|---|---|
| KMC05 | 11.9** | 84 |
| Control | 73.9 | — |

**Significant difference was noted on a 1% level to the control group by a t-test Taxonomic properties of KMC05 strain are as shown in the following Table 3.

TABLE 3

| Culture Temperature | 30° C. |
|---|---|
| Cell Form | *coccus* (1.0 µm diameter) |
| Gram staining | + |
| Spores | − |

TABLE 3-continued

| | | |
|---|---|---|
| Motility | – | |
| Colony Form | | Medium: MRS agar |
| | | Incubating time: 48 hours |
| | | Circular |
| | | All rims smooth |
| | | Slightly convex |
| | | With luster |
| | | Milky white color |
| Incubating | 37 | + |
| Temperature (° C.) | 45 | – |
| Catalase | | – |
| Oxidase | | – |
| Acid/Gas Production (glucose) | | +/– |
| O/F Test (glucose) | | +/+ |
| Biochemical Tests | Production of Acetoin | + |
| | Hydrolysis of Na Hippurate | + |
| | Hydrolysis of Aesculin | + |
| | Pyrrolidonylallylamidase | – |
| | α-Glactosidase | – |
| | β-Glucuronidase | – |
| | β-Galactosidase | + |
| | Alkaline Phosphatase | + |
| | Leucineallylamidase | + |
| | Arginine dihydrase | + |
| Fermentation Tests | D-Ribose | – |
| | L-Arabinose | – |
| | D-Mannitol | – |
| | D-Sorbitol | – |
| | Lactose | – |
| | D-Trehalose | – |
| | Inulin | – |
| | D-Raffinose | – |
| | Starch | – |
| | Glycogen | – |

From Table 3, KMC05 strain was presumed to be a strain belonging to the genus *Pediococcus* or the genus *Lactococcus* and, further, as a result of a 16SrDNA base sequence analysis, it was identified as a strain assigned to *Pediococcus pentosaceus*.

KMC05 strain has been deposited as follows in the name of Kyoto Prefectural Institute of Agricultural Biotechnology which is one of the organizations of Kyoto Prefecture (Head of the organization: Mr. Takakazu Namiki; address: 74 Kitainayazuma, Seika-cho, Souraku-gun, Kyoto 619-0244, Japan).

Name of depositary institution: International Patent Organism Depositary, National Institute of Advanced Industrial Science and Technology Address of depositary institution: AIST Tsukuba Central 6, 1-1, Higashi 1-chome, Tsukuba-shi, Ibaraki-ken 305-8566, Japan Date of deposit: Jun. 18, 2004 (Domestic accession date)

Accession number: FERM BP-10365 (internationally deposited on Jul. 1, 2005 from FERM P-20091 which was domestically deposited on Jun. 18, 2004)

In the meanwhile, other hopeful lactic acid bacteria which were selected together with KMC05 strain in the above secondary selection are as shown in the following Table 4, in which source of isolation for each of them is shown together with protective value.

TABLE 4

| Genus Species | Strain Name | Protective Value | Source of Isolation |
|---|---|---|---|
| Lactobacillus plantarum | MOE 07 | 41 | neonatal feces |
| Lactobacillus plantarum | MDK 13 | 44 | neonatal feces |
| Lactobacillus plantarum | WKB 19 | 42 | neonatal feces |
| Lactobacillus alimentarius | SHH 25 | 67 | neonatal feces |
| Lactobacillus sakei | KMC 11 | 41 | kimchi |
| Pediococcus pentosaceus | FM 54 | 42 | fermented milk |
| Pediococcus acidilactici | SHH 16 | 44 | neonatal feces |

Example 2

Control Effect on Damping-Off of Spinach

It was confirmed whether KMC05 strain selected as a lactic acid bacterium which suppresses Fusarium wilt of spinach had control effect on Damping-off which is another soil disease of spinach.

A microbe of Damping-off (OPU407 strain of *Pythium ultimum* obtained from Osaka Prefecture University) was used and it was cultured at 22° C. for two weeks on two media prepared from 1 g of spinach seeds and 5 ml of distilled water. The mycelia were ground with small amount of sterile soil and then made into 100 g with sterile soil to prepare an inoculum. The inoculum source was diluted to an extent of 200- and 300-fold with sterile soil and filled in a plastic pot of 10.5 cm diameter to give infested soil.

KMC05 strain was cultured at 37° C. for three days on 8 ml of an MRS liquid medium and then centrifuged to recover the cells. The recovered cells were washed with sterile water for three times and, in a suspension in a concentration of $10^9$ cfu/ml prepared with sterile water, seeds of spinach (variety name: Okame) in the same amount as the suspension were dipped at 23° C. for 24 hours. After that, the seeds subjected to a dipping treatment were sown in 12 pots to each infested soil of the above-mentioned 200- and 300-fold dilutions in 10 seeds per each pot and grown in a greenhouse where the lowest temperature was kept at 20° C. After six days from the sowing, germination was checked while, after 20 days from the sowing, damping-off was checked and Damping-off showing the rate of damping-off seedlings to germinated seedlings was determined. As a control group, seeds dipped in sterile water were used instead of a suspension of KMC05 strain.

TABLE 5

| Dilution Rate of Inoculum | Germinated Seedling (plants/pot) | | Percentage of damping-off seedling (%) | |
|---|---|---|---|---|
| | Control | KMC05 | Control | KMC05 |
| 200 | 4.7 | 9.2** | 62.7 | 31.8** |
| 300 | 8.8 | 9.2 | 32.8 | 16.3* |

*Significant difference was noted on a 5% level to the control group by a t-test
**Significant difference was noted on a 1% level to the control group by a t-test The result is as shown in Table 5 and, when treatment was conducted with KMC05 strain, pre-germination seed rot decreased and strains growing in a healthy state increased. With regard to germinated seedlings, percentage of damping-off also decreased.

Example 3

Improvement in Germination Rate of Spinach Seeds Under Conditions where Soil Water Contents were Excessive In order to confirm whether the aforementioned KMC05 strain has an effect of promoting the germination of seeds of agricultural crop under an environmental stress condition, KMC05 strain was cultured at 37° C. for 3 days in 8 ml of an MRS liquid medium and then centrifuged to recover the cells. The recovered cells were washed with sterile water for three times and, in a suspension in a concentration of $10^9$ cfu/ml prepared with sterile water, seeds of spinach (variety name: Okame) in the same amount as the suspension were dipped at 23° C. for 24 hours. After that, the seeds subjected to a dipping treatment were sown in ten plastic cups (each being in 600-ml volume) at the rate of 10 seeds per cup and grown in an incubator kept at 23° C. In the growing, water was drenched to make soil water contents 110%, 120% or 130% of the maximum water-holding capacity so as to make the state where soil water contents were excessive. After seven days form the sowing, germination was checked. Incidentally, as a control group, seeds dipped in sterile distilled water instead of in KMC05 strain suspension were used.

TABLE 6

| Soil water content | Germinated Seedling (plants/pot) | |
|---|---|---|
| (% of MWHC) | Control | KMC05 |
| 110 | 5.7 | 7.8* |
| 120 | 5.4 | 8.3* |
| 130 | 2.3 | 4.7* |

*Significant difference was noted on a 5% level to the control group by a t-test % of MWHC: Rate of soil water contents to the maximum water-holding capacity The result was as shown in Table 6 and, when treatment with KMC05 strain was conducted, germination rate of spinach seeds was able to be enhanced under an environmental stress condition. Accordingly, when a treatment with the KMC05 strain was conducted, not only a control effect on plant diseases was available but also germination rate of the seeds under an environmental stress condition was enhanced to give an effect for stabilizing the germination.

Example 4

Control Effect on *Phytophthora* Rot of Pepper

The aforementioned lactic acid bacterium KMC05 strain was subjected to a stationary culture at 30° C. for 3 days in 8 ml of an MRS liquid medium and then centrifuged at 5,000 rpm for 5 minutes to recover the cells. The recovered cells were washed with sterile water for three times and, in a suspension in a concentration of $10^9$ cfu/ml prepared with sterile water, seeds of pepper (variety name: Fushimi togarashi) in the same amount as the suspension were dipped at 23° C. for 24 hours. After that, the seeds subjected to a dipping treatment were sown in a cell tray filled with commercially available cultivating soil and grown at 30° C. for 40 days.

A pathogenic microbe (pph strain of *Phytophthora capsici*) was cultured at 23° C. for 10 days in 200 ml of a V8 liquid medium, then homogenized with V8 liquid medium and that was diluted with sterile water to an extent of 10-fold.

The seedlings grown on the cell tray were transplanted to a plastic pot of 10.5 cm diameter filled with commercially available cultivating soil and 20 ml of a liquid containing the ground pathogenic microbe prepared by the above-mentioned homogenization was drenched to the near part of the seedling. Incidentally, in a control group, seeds which were subjected to a dipping treatment with sterile water under the same condition were used. Twenty-four pots were used for each treatment.

After one month from the transplantation and the drenching of disease pathogenic microbe, disease severity index was checked. In checking disease severity index, healthy, little rot, medium rot, much rot and death were evaluated as 0, 1, 2, 3 and 4, respectively and disease severity and protective value were calculated by the following formulae.

$$\text{Disease severity} = (0 \times A + 1 \times B + 2 \times C + 3 \times D + 4 \times E)/(4 \times (A+B+C+D+E)) \times 100$$

In the formula, A, B, C, D and E are seedling numbers of healthy, little rot, medium rot, much rot and death, respectively.

$$\text{Protective value} = (1 - (\text{Disease severity in treatment})/(\text{Disease severity in control})) \times 100$$

TABLE 7

| Treatement | Disease severity | Protective Value |
|---|---|---|
| KMC05 | 8.3 | 78 |
| Control | 37.5 | — |

The result is as shown in Table 7 and, when the treatment with KMC05 strain was conducted, control effect on *Phytophthora* rot of pepper was apparently noted.

Example 5

Control Effect on Soft Rot of Vegetables 410 bacterial strains presumed to be mostly composed of lactic acid bacteria isolated from fermented milk or fermented foods were used and subjected to a primary selection. In the primary selection, each bacterium was subjected to a stationary culture on 8 ml of an MRS liquid medium at 30° C. for 2 days and then centrifuged at 5,000 rpm for 5 minutes to recover the cells. The recovered cells were washed with sterile water for three times, suspended in sterile water to make $10^9$ cfu/ml and a bacterium of soft rot (MAFF 302818 strain of *Erwinia carotovora*) was added thereto with an adjustment so as to make it $10^7$ cfu/ml. Eight cabbage leaf disks each having 1 cm diameter were dipped in the above suspension at 24° C. for 1 hour, water on the disk surfaces was removed and the disks were aligned on a 9-cm sterile culture dish and allowed to stand at 28° C. for 24 hours. In a control group, the disks were dipped in a liquid where the bacterium of soft rot was added to sterile distilled water so as to make it $10^7$ cfu/ml.

Diseased areas of 0%, 1 to 49%, 50 to 99% and 100% in each disk were evaluated as disease severity indexes of 0, 1, 2 and 3, respectively and disease severity and protective value were calculated by the following formulae. Twenty-seven strains where the protective value was 40 or more were selected as lactic acid bacteria having a control effect on plant diseases.

$$\text{Disease severity} = (0 \times A + 1 \times B + 2 \times C + 3 \times D)/(3 \times (A+B+C+D)) \times 100$$

In the formula, A, B, C and D are cabbage leaf disk numbers where diseased areas were 0%, 1 to 49%, 50 to 99% and 100%, respectively.

Protective value=(1−(Disease severity in treatment)/(Disease severity in control))×100

A secondary selection was conducted for the 27 strains which were selected in the primary selection as above. In the secondary selection, a liquid where the bacterium of soft rot was added to adjust to make it $10^7$ cfu/ml to a lactic acid bacterium suspension which was incubated by the same method as in the primary selection and adjusted to $10^8$ cfu/ml was used, and the same method as in the primary selection was conducted to select 9 strains showing a protective value of 40 or more.

After that, the nine strains were subjected to a third selection. In the third selection, a liquid where a bacterium of soft rot was added to adjust to make it $10^7$ cfu/ml to a lactic acid bacterium suspension which was incubated by the same method as in the primary selection and adjusted to $10^9$ cfu/ml. End of a bundle of ten sewing needles was dipped in the resulting suspension and subjected to a puncturing method to a midrib area of Chinese cabbage leaf (variety name: Muso) after 25 days from the sowing. The inoculation was conducted to three areas per seedling and to five seedlings for each treatment. In a control group, a liquid prepared so as to make same concentration of the bacterium of soft rot was used.

After ten days from the inoculation, disease severity was checked. In checking the disease severity index, only healthy state or mere darkening into brown color, less than 1 cm of diseased area and 1 cm or more diseased area were evaluated as 0, 1 and 2 for each inoculated site, and disease severity and protective value were calculated by the following formulae.

Disease severity=(0×A+1×B+2×C)/(2×(A+B+C))×100

In the formula, A, B and C are inoculated site numbers where there was only healthy state or mere darkening into brown color, less than 1 cm of diseased area and 1 cm or more diseased area, respectively.

Protective value=(1−(Disease severity in treatment)/(Disease severity in control))×100

As a result, three strains as a lactic acid bacterium being effective to soft rot of Chinese cabbage were selected and, among them, SHH15 strain particularly good in the control effect was selected. Disease severity and protective value of SHH15 strain were as shown in the following Table 8.

TABLE 8

| Treatment | Disease severity | Protective Value |
|---|---|---|
| SHH15 | 3.3 | 95 |
| Control | 66.7 | — |

From the result of a base sequence analysis of 16SrDNA, SHH15 strain was identified as a strain assigned to *Lactobacillus plantarum*. SHH15 strain has been deposited as follows in the name of Kyoto Prefectural Institute of Agricultural Biotechnology which is one of the organizations of Kyoto Prefecture (Head of the organization: Mr. Takakazu Namiki; address: 74 Kitainayazuma, Seika-cho, Souraku-gun, Kyoto 619-0244, Japan).

Name of depositary institution: Incorporated Administrative Agency, National Institute of Technology and Evaluation, Patent Microorganisms Depositary Address of depositary institution: 2-5-8 Kazusakamatari, Kisarazu-shi, Chiba-ken, 292-0818, Japan Date of deposit: Jun. 30, 2005

Accession number: NITE BP-108

As shown in Table 8, SHH15 strain had a good control effect on soft rot of Chinese cabbage and, as a result of treatment with that, soft rot of Chinese cabbage was apparently suppressed.

Incidentally, other favorable lactic acid bacteria selected together with SHH15 strain in the above-mentioned third selection are as shown in the following Table 9 and source of isolation for each of them is shown together with its protective value.

TABLE 9

| Genus/Species | Strain Name | Protective Value | Source of Isolation |
|---|---|---|---|
| *Lactobacillus plantarum* | RK01 | 70 | scallion |
| *Lactobacillus plantarum* | SHH28 | 95 | neonatal feces |

Example 6

Enhancement of Germination Rate of Spinach Seeds Under the Condition where Soil Water Content was Excessive In order to confirm whether the above-mentioned lactic acid bacterium SHH15 strain has an effect of promoting the germination of agricultural crop under an environmental stress condition, SHH15 strain was cultured in 8 ml of an MRS liquid medium at 30° C. for 3 days and then centrifuged to recover the cells. The recovered cells were washed with sterile water for three times and, in a suspension in a concentration of $10^9$ cfu/ml prepared with sterile water, seeds of spinach (variety name: Okame) in the same amount as the suspension were dipped at 24° C. for 24 hours. After that, the seeds subjected to a dipping treatment were sown in ten plastic cups (each being in 600-ml volume) at the rate of 10 seeds per cup and grown in an incubator kept at 25° C. In the growing, water was drenched to make soil water content 120% of the maximum water-holding capacity so as to give the state where soil water content was excessive. After seven days form the sowing, germination was checked. Incidentally, as a control group, seeds dipped in sterile distilled water instead of in SHH15 strain suspension were used.

TABLE 10

| Treatment | Germinated Seedling (plants/pot) |
|---|---|
| SHH15 | 6.2** |
| Control | 3.4 |

**Significant difference was noted on a 1% level to the control group by a t-test The result is as shown in Table 10 and, by the treatment with SHH15 strain, germination rate of spinach seeds under an environmental stress condition was able to be enhanced. Accordingly, when a treatment with SHH15 strain was conducted, not only a control effect on plant disease was available but also germination rate of the seeds under an environmental stress condition was enhanced to give an effect for stabilizing the germination.

INDUSTRIAL APPLICABILITY

The controlling agent and the controlling method for plant disease in accordance with the present invention are able to control the plant disease using lactic acid bacteria which are seemingly advantageous to human health whereby they are able to contribute in safe and stable production of agricultural crop.

The invention claimed is:

1. A plant disease controlling agent comprising a plant disease controlling amount of a biologically pure culture of a lactic acid bacterium that is capable of controlling plant disease caused by at least one pathogenic microorganism selected from the group consisting of *Pythium ultimum, Phytophthora capsici* and *Erwinia carotovora*, wherein the lactic acid bacterium is at least one microorganism selected from the group consisting of *Pediococcus pentosaceus* FERM BP-10365 and *Lactobacillus plantarum* NITE BP-108.

2. A method of controlling a plant disease caused by *Pythium ultimum, Phytophthora capsici* and/or *Erwinia carotovora*, comprising treating at least one of plant or soil with a lactic acid bacterium that is capable of controlling plant disease caused by at least one pathogenic microorganism selected from *Pythium ultimum, Phytophthora capsici* and *Erwinia carotovora*, wherein the lactic acid bacterium is at least one microorganism selected from the group consisting of *Pediococcus pentosaceus* FERM BP-10365 and *Lactobacillus plantarum* NITE BP- 108.

3. The plant disease controlling agent of claim 1, further comprising a pharmaceutically acceptable carrier.

4. The plant disease controlling agent of claim 3, wherein the pharmaceutically acceptable carrier is selected from diatomaceous earth, clay, talc, perlite, chaff, and bone powder.

* * * * *

UNITED STATES PATENT AND TRADEMARK OFFICE
CERTIFICATE OF CORRECTION

PATENT NO. : 8,568,710 B2  
APPLICATION NO. : 11/658544  
DATED : October 29, 2013  
INVENTOR(S) : Kazuhisa Tsuda et al.

It is certified that error appears in the above-identified patent and that said Letters Patent is hereby corrected as shown below:

On the Title Page Item (73) should read,

(73) Assignee:  --Kyoto Prefecture, Kyoto-shi (JP)--

Meiji Seika Pharma Co., Ltd., Tokyo (JP)

Signed and Sealed this  
Sixth Day of May, 2014

Michelle K. Lee  
*Deputy Director of the United States Patent and Trademark Office*